United States Patent
Mokhtee

(10) Patent No.: US 9,044,843 B1
(45) Date of Patent: Jun. 2, 2015

(54) STRIP RESISTANT SCREW AND RESCUE DRIVER

(71) Applicant: David Mokhtee, Broken Arrow, OK (US)

(72) Inventor: David Mokhtee, Broken Arrow, OK (US)

( * ) Notice: Subject to any disclaimer, the term of this patent is extended or adjusted under 35 U.S.C. 154(b) by 0 days.

(21) Appl. No.: 14/271,573

(22) Filed: May 7, 2014

(51) Int. Cl.
  *B25B 23/00* (2006.01)
  *B25B 15/00* (2006.01)
  *B25B 15/02* (2006.01)
  *A61B 17/86* (2006.01)
  *A61B 17/88* (2006.01)
  *F16B 23/00* (2006.01)

(52) U.S. Cl.
  CPC ............... *B25B 15/004* (2013.01); *B25B 15/02* (2013.01); *A61B 17/8615* (2013.01); *A61B 17/888* (2013.01); *F16B 23/0084* (2013.01)

(58) Field of Classification Search
  CPC ...... B25B 15/006; B25B 15/00; B25B 15/04; B25B 13/48; B25B 13/486; B25B 27/0071; F16B 23/0023; F16B 23/003; F16B 23/00; F16B 23/0007; F16B 23/0062; F16B 23/0076; F16B 23/0084; F16B 23/0092; A61B 17/8615; A61B 17/88
  USPC .......................... 81/451, 459, 460, 461, 53.2; 411/403–405, 407, 408, 410, 378; D8/82, 86, 349, 382, 387
  See application file for complete search history.

(56) References Cited

U.S. PATENT DOCUMENTS

| | | | | |
|---|---|---|---|---|
| 422,307 | A * | 2/1890 | Libbey | 411/412 |
| 2,140,449 | A * | 12/1938 | Brown | 411/410 |
| 2,173,707 | A * | 9/1939 | Brown | 411/403 |
| 2,800,829 | A * | 7/1957 | West | 411/404 |
| 3,463,209 | A * | 8/1969 | Podolsky | 81/436 |
| 3,675,694 | A * | 7/1972 | Barlow | 81/460 |
| 3,695,321 | A | 10/1972 | Garehime, Jr. | |
| 3,872,904 | A | 3/1975 | Barlow | |
| D264,552 | S * | 5/1982 | Bogren | D8/387 |
| 4,339,971 | A * | 7/1982 | Zatorre | 81/436 |
| 4,497,225 | A | 2/1985 | Vaughn | |
| 4,538,486 | A * | 9/1985 | Lutrat | 81/460 |
| 4,900,208 | A * | 2/1990 | Kaiser et al. | 411/387.1 |
| 4,936,172 | A | 6/1990 | Jackson | |
| D322,928 | S * | 1/1992 | Snodell | D8/387 |
| D334,336 | S * | 3/1993 | Terrels et al. | D8/387 |
| 5,353,667 | A * | 10/1994 | Wilner | 81/436 |
| 5,358,368 | A * | 10/1994 | Conlan et al. | 411/410 |
| 5,438,895 | A | 8/1995 | Bassell et al. | |
| 5,498,265 | A | 3/1996 | Asnis et al. | |
| 5,868,049 | A | 2/1999 | Kanwal | |
| 6,128,983 | A * | 10/2000 | Arnn | 81/460 |

(Continued)

*Primary Examiner* — Lee D Wilson
*Assistant Examiner* — Melanie Alexander
(74) *Attorney, Agent, or Firm* — Molly D. McKay

(57) ABSTRACT

A screw with a head that includes a flat area with a first indented area located centrally within the head and a second indented area located centrally within the first indented area, and all three areas provided with grooves for engagement with tools. A screw driver having mating ridges that insert within the grooves on the first indented area rotates the screw to insert it into a substrate. A rescue driver engages the grooves of the flat head and second indented area to remove the screw from the substrate when the grooves in the first indented area become stripped. The head of an alternate screw is provided centrally with a reverse threaded female channel engagable by a reverse threaded rescue driver to remove the screw from a substrate when the grooves in the alternate screw's head that are used to insert the screw into a substrate become stripped.

2 Claims, 2 Drawing Sheets

(56) References Cited

U.S. PATENT DOCUMENTS

| | | |
|---|---|---|
| 6,378,406 B1 | 4/2002 | Totsu |
| 6,886,433 B2 * | 5/2005 | Totsu ............................... 81/460 |
| 6,988,432 B2 * | 1/2006 | Brooks ........................... 81/439 |
| D524,638 S * | 7/2006 | Berhow ........................ D8/387 |
| 7,165,482 B2 | 1/2007 | Shapoval |
| 7,311,026 B2 | 12/2007 | Melton |
| 7,325,469 B1 * | 2/2008 | Clampitt et al. ................. 81/436 |
| 8,623,019 B2 | 1/2014 | Perrow et al. |
| 2001/0004694 A1 * | 6/2001 | Carchidi et al. ................. 606/73 |
| 2003/0053887 A1 * | 3/2003 | Brooks ......................... 411/403 |
| 2003/0059276 A1 * | 3/2003 | Chen ............................. 411/403 |
| 2005/0047891 A1 * | 3/2005 | Toyooka et al. ............... 411/403 |
| 2005/0216015 A1 * | 9/2005 | Kreidler .......................... 606/73 |
| 2007/0193419 A1 * | 8/2007 | Melton ........................... 81/436 |

* cited by examiner

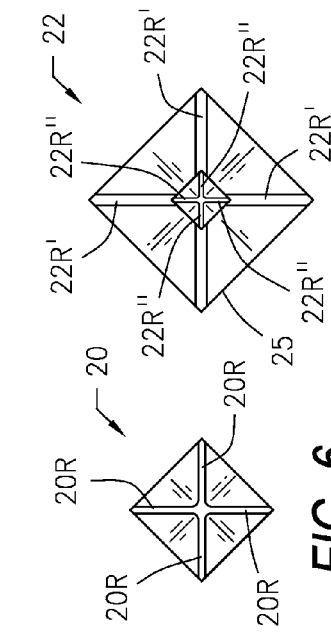
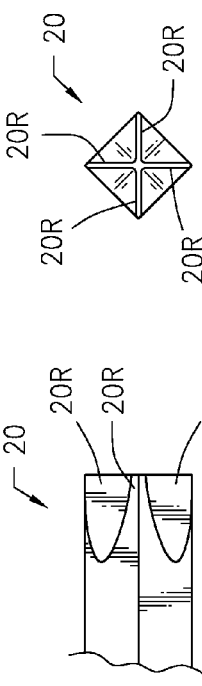
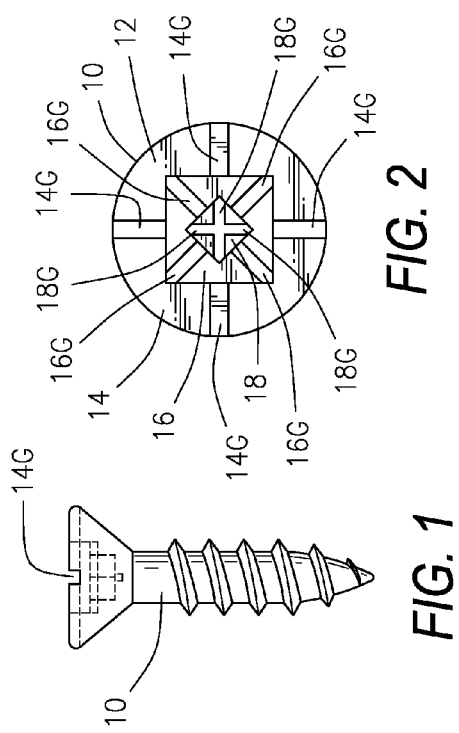
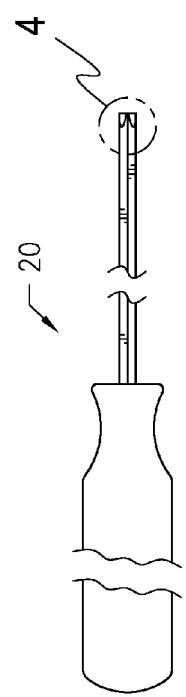
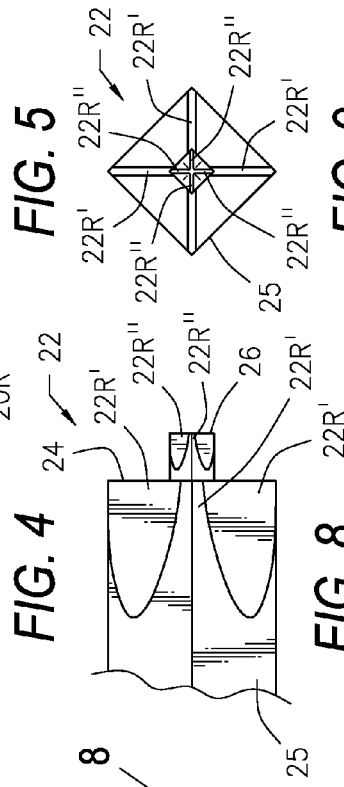
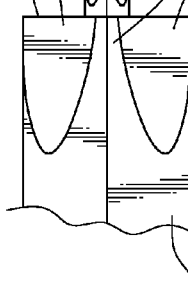
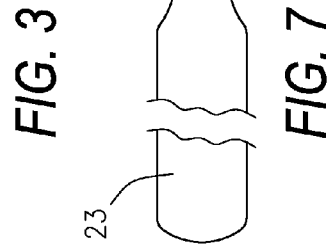

STRIP RESISTANT SCREW AND RESCUE DRIVER

BACKGROUND OF THE INVENTION

1. Field of the Invention

The present invention is a screw for use with a screw driver for inserting the screw into a substrate and a rescue driver for removing the screw from the substrate when it becomes stripped such that it cannot be removed from the substrate employing the screw driver.

2. Description of the Related Art

Currently, when a screw becomes stripped, it becomes difficult or impossible to remove the screw from the substrate in which it is fastened. In surgical applications, it would be desirable to be able to remove a stripped screw from the substrate in which it is fastened, such as for example from a bone in the human body.

The present invention addresses this need by providing a first embodiment screw and an alternate embodiment screw that are both capable of being removed from a substrate with a rescue driver after the screw has become stripped such that the screw driver that was used to install the screw in the substrate cannot be employed to remove the screw.

The first preferred embodiment of the invention employs a screw with a screw head that includes the normal head with a first indented area located centrally within the head and a second indented area located centrally within the first indented area. The normal head, the first indented area and the second indented area each is provided with grooves for engagement with a tool. The grooves provided on the first indented area are engagable by a screw driver specifically matched to the screw such that the screw driver is provided with mating ridges that insert within and engage the grooves of the first indented area so that the screw can be inserted into a substrate employing the screw driver.

The grooves provided on the normal head and on the second indented area are engagable by a rescue tool or rescue driver specifically matched to the screw such that the rescue driver is provided with mating ridges that insert within and engage the grooves of the normal head and the second indented area so that the screw can be removed from a substrate employing the rescue driver when the grooves provided in the first indented area become stripped so that the screw cannot be removed from the substrate employing the screw driver.

A second embodiment of the invention employs a screw that is provided externally with normal threads and the head of the screw is provided with a central female threaded channel that is reverse threaded from the external threads of the screw. A normal screw driver is used to install the screw in a substrate by engaging grooves provided in the head of the screw with mating ridges on the screw driver. In order to remove the alternate screw from a substrate when the grooves in its head become stripped, a reverse threaded rescue tool is used. The reverse threaded rescue tool inserts into the central female threaded channel and is rotated to engage the reverse threads of the channel. The reverse threaded rescue tool is tightened into the channel until it is fully engaged with the female threaded channel. At that point, the screw will rotate in conjunction with the rescue tool to back the screw out of the substrate.

SUMMARY OF THE INVENTION

The first embodiment of the invention employs a screw with a screw head that includes the normal head with a first indented area located centrally within the head and a second indented area located centrally within the first indented area. The normal head, the first indented area and the second indented area each is provided with grooves for engagement with a tool. The grooves provided on the first indented area are engagable by a screw driver specifically matched to the screw such that the screw driver is provided with mating ridges that insert within and engage the grooves of the first indented area so that the screw can be inserted into a substrate employing the screw driver.

The grooves provided on the normal head and on the second indented area are engagable by a rescue tool or rescue driver specifically matched to the screw such that the rescue driver is provided with mating ridges that insert within and engage the grooves of the normal head and the second indented area so that the screw can be removed from a substrate employing the rescue driver when the grooves provided in the first indented area become stripped so that the screw cannot be removed from the substrate employing the screw driver.

A second embodiment of the invention employs a screw that is provided externally with normal threads and the head of the screw is provided with a central female threaded channel that is reverse threaded from the external threads of the screw. A normal screw driver is used to install the screw in a substrate by engaging grooves provided in the head of the screw with mating ridges on the screw driver. In order to remove the alternate screw from a substrate when the grooves in its head become stripped, a reverse threaded rescue tool is used. The reverse threaded rescue tool inserts into the central female threaded channel and is rotated to engage the reverse threads of the channel. The reverse threaded rescue tool is tightened into the channel until it is fully engaged with the female threaded channel. At that point, the screw will rotate in conjunction with the rescue tool to back the screw out of the substrate.

BRIEF DESCRIPTION OF THE DRAWINGS

FIG. 1 is a side view of a screw that is constructed in accordance with a preferred first embodiment of the present invention.

FIG. 2 is a top plan view of the head of the screw of FIG. 1 showing the indented areas and grooves.

FIG. 3 is a perspective view of a screw driver that is employed to secure the screw of FIGS. 1 and 2 to a substrate.

FIG. 4 is an enlarged view of the tip of the screw driver that is shown within circle 4 of FIG. 3.

FIG. 5 is a front end view of the tip of FIG. 4.

FIG. 6 is a further enlarged view of the tip of FIG. 5 showing the ridges.

FIG. 7 is perspective view of a rescue driver that is employed to remove the screw of FIGS. 1 and 2 from a substrate when the screw has become stripped and cannot be removed with a screw driver.

FIG. 8 is an enlarged view of the tip of the rescue driver that is shown within circle 8 of FIG. 7.

FIG. 9 is a front end view of the tip of FIG. 48.

FIG. 10 is a further enlarged view of the tip of FIG. 9 showing the ridges.

DETAILED DESCRIPTION OF THE PREFERRED EMBODIMENT

Figure 13:
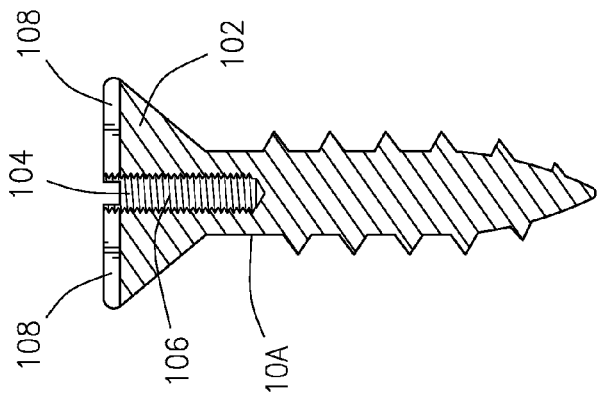
FIG. 13 is a cross sectional view of the alternate screw taken along line 13-13 of FIG. 12 to show the central female reverse threaded channel.

Referring now to the drawings and initially to FIGS. 1 and 2, there is illustrated a screw 10 that is constructed in accordance with a preferred embodiment of the present invention. The screw 10 has a screw head 12 that includes a normal flat head area 14 with a first indented area 16 located centrally within the head 12 and a second indented area 18 located centrally within the first indented area 16. The flat head area 14, the first indented area 16 and the second indented area 18 each is provided with several grooves 14G, 16G and 18G for engagement with tools 20 and 22, as will be more fully explained hereafter.

Referring also to FIGS. 3-6, the grooves 16G provided on the first indented area 16 are engagable by a screw driver 20 specifically matched to the screw 10 such that the screw driver 20 is provided with mating ridges 20R that insert within and engage the grooves 16G of the first indented area 16 so that the screw 10 can be inserted into a substrate employing the screw driver 20 to rotate the screw 10 in a right handed or clockwise manner.

Referring now also to FIGS. 7-10, the grooves 14G provided on the flat head area 14 and the grooves 18G provided on the second indented area 18 are engagable by a rescue tool or rescue driver 22 specifically matched to the screw 10 such that the rescue driver 22 is provided with two sets of mating ridges 22R' and 22R" provided respectively on a first flat face 24 of the rescue driver 22 and on a central protruding second face 26 of the rescue driver 22. The ridges 22R' on the first flat face 24 and the ridges 22R" on the central protruding second face 26 insert within and engage, respectively, the grooves 14G of the flat head area 14 and the grooves 18G of the second indented area 18 so that the screw 10 can be removed from a substrate employing the rescue driver 22 when the grooves 16G provided in the first indented area 16 become stripped so that the screw 10 cannot be removed from the substrate employing the screw driver 20. The rescue driver 22 is used to rotate the screw 10 in a reverse, left handed or counterclockwise direction to remove the screw 10 from the substrate.

Figure 12:
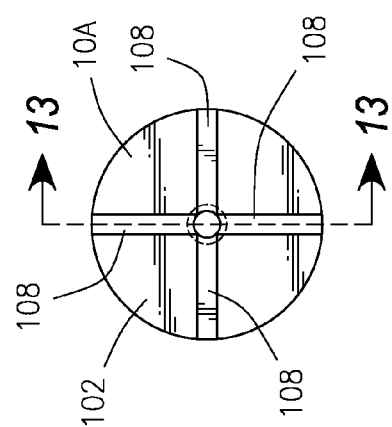
FIG. 12 is a top plan view of the head of the alternate screw of FIG. 11.
Figure 11:
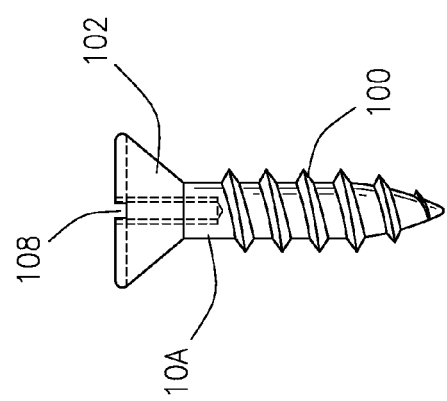
FIG. 11 is a side view of second screw that is constructed in accordance with an alternate embodiment of the present invention.

Referring now to FIGS. 11-13, there is illustrated an alternate screw 10A that is a second or alternate embodiment of the invention. The alternate screw 10A that is provided externally with normal right handed threads 100 and the head 102 of the alternate screw 10A is provided with a central female threaded channel 104 that is reverse threaded from the external threads of the alternate screw 10A. Thus, the threads 106 of the channel 104 are left handed threads.

A screw driver such as the screw driver 20 that is illustrated in FIGS. 3-6, is used to install the alternate screw 10A in a substrate by engaging grooves 108 provided in the head 102 of the alternate screw 10A with mating ridges 20R on the screw driver 20.

Figure 15:
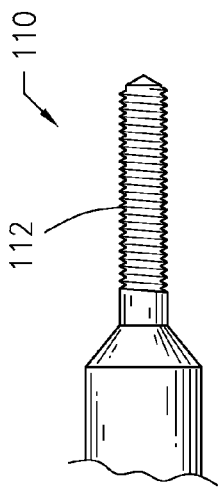
FIG. 15 is an enlarged view of the tip of the alternate rescue driver that is shown within circle 15 of FIG. 14.
Figure 14:
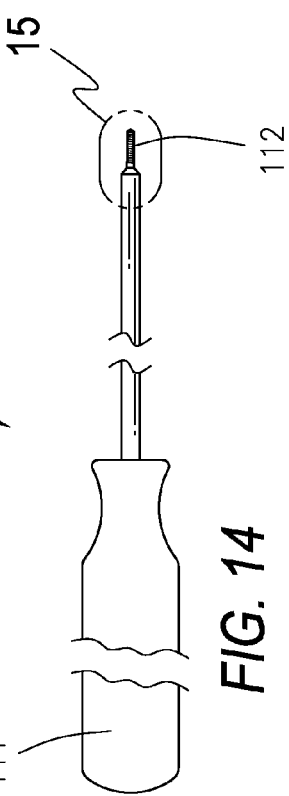
FIG. 14 is an alternate rescue driver for use with the alternate screw of FIGS. 11 and 12.

Referring also to FIGS. 14 and 15, in order to remove the alternate screw 10A from a substrate when the grooves 108 in its head 102 become stripped so that the screw driver 20 of FIGS. 3-6 cannot be used to remove the alternate screw 10A, a reverse threaded rescue tool 110 is used. The reverse threaded rescue tool 110 has a male threaded end 112 that inserts into the central female threaded channel 104 and is rotated counterclockwise to engage the reverse threads 106 of the channel 104. The reverse threaded rescue tool 110 is tightened into the female threaded channel 104 until it is fully engaged with the channel 104. At that point, the alternate screw 10A will rotate in conjunction with the rescue tool 110 in a left handed or counterclockwise direction to back the alternate screw 10A out of the substrate.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. A strip resistant screw and rescue driver combination comprising:
   a screw with a screw head that includes a flat head area with a first indented area located centrally within the flat head area of the head and a second indented area located centrally within the first indented area,
   grooves provided in each of the three areas of the head,
   said grooves provided in the first indented area that are engagable by mating ridges provided on a screw driver for inserting the screw into a substrate,
   said grooves provided in the flat head area and in the second indented area that are engagable by mating ridges provided on a rescue driver.

2. The strip resistant screw and rescue driver combination of claim 1, comprising:
   the rescue driver comprising;
   a handle to which a driving head is attached,
   said driving head provided with ridges on a first flat face of the rescue driver which are engagable with the grooves of the flat head area of the strip resistant screw, and
   said driving end provided with ridges on a central protruding second face of the rescue driver such that the ridges on the central protruding second face of the rescue driver are engagable with the grooves of the second indented area of the strip resistant screw so that the ridges on the driving head provide a means of removing the screw from a substrate.

* * * * *